United States Patent [19]

Shaw

[11] Patent Number: 5,206,439
[45] Date of Patent: Apr. 27, 1993

[54] PREPARATION OF HIGH PURITY POLYSULFIDES

[75] Inventor: James E. Shaw, Bartlesville, Okla.

[73] Assignee: Phillips Petroleum Company, Bartlesville, Okla.

[21] Appl. No.: 826,356

[22] Filed: Jan. 27, 1992

[51] Int. Cl.$^5$ .......................................... C07C 321/14
[52] U.S. Cl. .......................................... 568/21; 568/26
[58] Field of Search ................................... 568/21, 26

[56] References Cited

U.S. PATENT DOCUMENTS 3,022,351  2/1962  Mihin et al. .................... 260/608
3,308,166  3/1967  Biensan et al. .................. 260/608

FOREIGN PATENT DOCUMENTS 0025944  11/1980  European Pat. Off. ............. 149/12
58-140063  8/1983  Japan .............................. 149/12

OTHER PUBLICATIONS

Reil, E. E., Organic Chemistry of Bivalent Sulfur, Ch. 2 pp. 107–169.

Primary Examiner—Marianne M. Cintins
Assistant Examiner—Margaret Page
Attorney, Agent, or Firm—Gary L. Haag

[57] ABSTRACT

Product from the reaction of mercaptan with sulfur in the presence of a basic catalyst is treated by contacting with an alcohol-based solution containing an oxidizing agent and an inorganic basic catalyst followed by the recovery of a purified polysulfide product.

32 Claims, No Drawings

PREPARATION OF HIGH PURITY POLYSULFIDES

This invention relates to the preparation of high purity and highly stable polysulfides.

Organic polysulfides and particularly dialkyl polysulfides such as tetra- and penta-sulfides have been found useful for many purposes such as additives for elastomers, antioxidants for lubricating oils, intermediates for the production of organic chemicals, insecticides, germicides and as an additive to diesel fuels to improve the cetane number and ignition qualities of these fuels. These compounds have also been found useful in the compounding of extreme pressure lubricants and in the acceleration of rubber treating processes.

Methodologies are known in the art for the preparation of polysulfides by the reaction of elemental sulfur with mercaptans in the presence of a basic catalyst (European Patent 25 944) or a basic catalyst with an alcohol promoter (U.S. Pat. Nos. 3,308,166 and 3,022,351). However, problems associated with product degradation are frequently observed for polysulfide product containing 3 or greater sulfur atoms per polysulfide molecule. This degradation can cause the product appearance to change from a clear yellow or orange to a cloudy appearance and ultimately, precipitation will result. Furthermore, the presence of mercaptan and hydrogen sulfide in the polysulfide product causes a very undesirable odor which end users desire to have absent.

Methodologies are known in the art for the purification of the polysulfide product, but the absolute degree of purification is not well documented.

European Patent Application EP 25 944 discloses polysulfide purification by nitrogen purging the polysulfide product and then contacting said product with an amine-bearing, hydrogen peroxide-bearing aqueous solution at designated conditions followed by steam stripping and contacting with diatomaceous earth.

Kamii et al. (Japanese Application 58-140,063) discloses a method for deodorizing dialkyl polysulfides by contacting the polysulfide-bearing fluid with 1,2 epoxy compounds. The 1,2 epoxy compounds apparently react directly with the unreacted mercaptan and hydrogen sulfide, thereby producing a product with negligible odor. Excess 1,2 epoxy compounds are reportedly removed by conventional methods, such as vacuum distillation.

Diensan et al. (U.S. Pat. No. 3,308,166) discloses the preparation of polysulfides using an amine-catalyst and alcohol promoter. The alcohol is removed from the product stream by distillation and the amine catalyst by distillation and steam stripping. Water in the polysulfide product is then removed with sodium sulfate absorbent followed by the removal of residual hydrogen sulfide with bone black.

SUMMARY OF THE INVENTION

It is an object of this invention to provide a method for producing a high purity polysulfide.

A further object is to provide a method for producing a polysulfide product which does not degrade with time.

Yet a further object of this invention is to provide a novel method of producing polysulfide product containing an average of 3 to 6 sulfur atoms per polysulfide molecule.

A still further object of this invention is to provide a novel method for producing a polysulfide produce which does not possess the undesirable odor associated with mercaptans and hydrogen sulfide.

It is yet a further object of this invention to provide a stable polysulfide product.

In accordance with this invention, product from the reaction of mercaptan with sulfur in the presence of a basic catalyst is treated by contacting with an alcohol-based solution containing an oxidizing agent and an inorganic basic catalyst followed by the recovery of a purified polysulfide product.

DETAILED DESCRIPTION OF THE INVENTION

The preparation of the highly stable polysulfide product of this invention is a two step process. These two steps are (a) the reaction of mercaptan with elemental sulfur in the presence of a basic catalyst to form the polysulfide crude product and (b) treatment of this crude product to remove species which apparently promote long term polysulfide degradation. The first step in the process, that is the reaction of mercaptans with elemental sulfur in the presence of a basic catalyst to form a polysulfide product, is generally known in the art. However, the second step or the product treatment step enables an improvement on the prior art to be made.

Key attributes of the new process are the ability to produce a polysulfide product generally containing an average of 3 to 6 sulfur atoms in high yield which degrades minimally over extended time periods. Minimal degradation is accomplished by a unique treatment process wherein chemical species, most notably unreacted mercaptans and catalysts which apparently promote degradation, are selectively removed from the polysulfide crude product.

The crude polysulfide products are obtained by a reaction which can be depicted as follows:

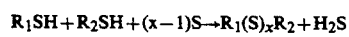

$$R_1SH + R_2SH + (x-1)S \rightarrow R_1(S)_xR_2 + H_2S$$

$R_1$ and $R_2$ are alkyl radicals, generally containing 1 to 20 carbon atoms, more preferably 4 to 18 carbon-atom tertiary alkyl radicals, and most preferably 9 to 12 carbon-atom tertiary alkyl radicals. $R_1$ and $R_2$ can be the same or different. In the preceding equation, x is the average number of sulfur atoms per polysulfide molecule in the crude product. The invention is broadly applicable to any polysulfide product produced in the presence of a basic catalyst. Preferably, it is applicable to those having an average sulfur atom number per polysulfide molecule of 2 through 8, and most preferably to those having an average sulfur atom number per polysulfide molecule of 3 through 6.

The procedure to prepare crude polysulfide product consists generally of adding one of the reactants, either the mercaptan or sulfur, slowly to the other reactant in the presence of a basic catalyst. The order of reactant addition does not have a significant effect on the final product. However, the preferred method is to slowly add sulfur to the mercaptan/catalyst solution. The sulfur, upon addition, readily dissolves in the solution. Mixing of the solution and/or operating at greater than ambient temperatures will enhance the reaction rate. The amount of sulfur to be added is dependent on the desired sulfur content of the polysulfide product. For an average sulfur content of x-sulfurs per polysulfide molecule, (x−1) moles of sulfur must be added and 1 mole of hydrogen sulfide will be released per 2 moles of mercaptan reacted. The catalyst should be basic in nature. Preferable catalyst include the primary, secondary, and tertiary alkyl and cycloaliphatic amines and the alkali metal and alkaline earth oxides and hydroxides. Most preferred are the tertiary alkylamines, particularly triethylamine. The weight of catalyst as a percentage of the weight of mercaptan should be 0.05 to 5%, preferably 0.1 to 2.0%, and most preferably 0.2 to 1.0%. Significant amounts of the reaction product, hydrogen sulfide, will be released as a gas during the reaction. Following completion of the reaction, residual hydrogen sulfide may be removed from the crude polysulfide product by heating, an inert gas purge or by vacuum stripping. When using an inert gas purge, preferable gases are nitrogen and air.

The second step in the preparation of highly stable polysulfides is the novel treatment process wherein a product possessing acceptable appearance, minimal odor, and which degrades minimally with time is obtained. This process apparently removes species from the crude product which promote long term polysulfide degradation. When present, this degradation may be observed by changes in the product odor, color, the transparency/opacity of the product, and the presence of a precipitate. A key factor in the selection of this process methodology was the observation that small quantities of unreacted mercaptan and catalyst apparently have a detrimental effect on the long term appearance and stability of the polysulfide product. The herein disclosed process was specifically tailored for the removal of these species.

An additional key factor in the development of this inventive process was the unexpected observation that when crude polysulfide product is thoroughly contacted with an alcohol-based wash fluid containing an oxidizing agent and an inorganic basic catalyst, the lower polysulfide-bearing phase on separation and drying is clear, possesses negligible odor, and is effectively stabilized for long term storage.

As an example, when the wash fluid comprises methanol as the alcohol, aqueous hydrogen peroxide as the oxidizing agent, and sodium hydroxide as the catalyst at 45° C., the mercaptan sulfur concentration in the polysulfide is typically less than 10 ppm by weight and a clear yellow product obtained (See Examples, particularly Example 2, Run No. 4). These results are surprising in light of other test results (See Example II and Table I). In one such test (Run No. 1), a hydrogen peroxide wash was conducted at 45° C. in the absence of alcohol and catalyst. The mercaptan sulfur content for the product was 460 ppm by weight and the product was unacceptably hazy and a precipitant was observed. In another test using a methanol/hydrogen peroxide wash fluid without a catalyst (Run No. 2), the results were variable in nature and generally 230 to 750 ppm by weight mercaptan sulfur was observed in the product and the product was visually unacceptable. No significant difference in results were observed whether the wash step was conducted for 4 hours at 45° C. (Run No. 2) or 4 hours at 68°-70° C. (Run No. 5). In product was 67 ppm by weight and the product was also hazy in appearance and a precipitant was observed.

Although wishing not to be bound by theory, the basic metal catalyst apparently catalyzes the oxidation of (1) unreacted mercaptan to disulfide, (2) hydrogen sulfide to sulfate, and (3) amine catalyst to amine oxide. Again, wishing not to be bound by theory, the alcohol apparently enables better solubilization of mercaptan, polysulfide and water into the alcoholic phase, thereby promoting the oxidation reactions and further serving as the preferred phase for the unreacted oxidizing agent (ex. hydrogen peroxide) and for various reaction products which are potential polysulfide contaminants (ex. water, amine oxides, hydrogen sodium sulfate and sodium sulfate). When the solubility limits for the sulfate reaction product are exceeded in the alcohol phase, precipitation results. This precipitation can occur either during the primary contacting of crude polysulfide with the alcohol-based fluid or during a subsequent drying step for the removal of residual alcohol and water present in the washed polysulfide. In either situation, the precipitated sulfate can be effectively removed by solids separation technique established in the art, such as filtration.

The wash fluid is comprised of an alcohol, an oxidizing agent, and an inorganic basic catalyst. The order of component addition in preparing the wash fluid is not critical. Indeed, the wash fluid components can be added directly to the crude polysulfide product in any order thereby forming a wash phase. However, because of the exothermic nature of the associated oxidation reactions and to maintain adequate temperature control, the preferred procedure is to first combine the alcohol and basic metal catalyst, combine this mixture with the crude polysulfide product and heat to the desired process temperature (typically 45° C.), and then incrementally add the oxidizing agent while thoroughly mixing the two phases. In another preferred embodiment, both the crude polysulfide phase and the wash solution which consists of an alcohol, oxidizing agent, and basic metal catalyst are individually brought to the desired process temperature and the wash fluid then incrementally added while thoroughly mixing the two phases. In still another preferred embodiment, the inorganic basic catalyst is first dissolved in water and then it and the alcohol are each added to the crude polysulfide phase. The oxidizing agent is then incrementally added to this mixture. It is desirable that the volume of the spent wash fluid which is a waste stream be minimized. A crude polysulfide to wash fluid weight ratio of greater than 3:1 is preferred, 6:1 to 20:1 more preferred and about 9:1 to about 15:1 most preferred.

The wash fluid is alcohol-based. The lower molecular weight alcohols are generally preferred, because they are excellent mercaptan/water solubilizers and possess relatively high vapor pressures. Higher vapor pressures simplify the subsequent removal of residuals, such as water and alcohol from the washed polysulfide phase. Residuals are removed by a drying step which can consist of vacuum stripping, gas purging, heating, or flowing the washed polysulfide phase through a suitable sorbent bed. Vacuum stripping and gas purging at elevated temperatures are preferred over heating because they are more effective and preferred over sorbent bed drying because of waste disposal considerations. The $C_1$–$C_5$ alcohols are preferred because of their solubilization properties. The $C_1$–$C_3$ are more preferred because of their respectively greater vapor pressures. Methanol is most preferred because of its combined solubilization properties, high vapor pressure, and lower density thus providing a greater density contrast between the alcohol-phase and the polysulfide phase, thereby simplifying the phase separation step following the crude polysulfide wash.

The oxidizing agent must have some solubility in alcohol, negligible solubility in polysulfides, and sufficient oxidation capacity toward hydrogen sulfide, amines, and mercaptan so as to render the polysulfide product stream stable. Oxidizing agents as used herein include but are not limited to peracids, hypochlorites, persulfates, hydroperoxides, organic peroxides, oxygen, ozone and hydrogen peroxide. Most preferred is hydrogen peroxide because of its reactivity, ready availability, ease of handling and cost.

The process requires an inorganic basic catalyst. Preferred catalysts are alkali metal and alkaline earth carbonates. More preferred catalyst are the alkali metal and alkaline earth oxides because of their greater catalytic activity. Still more preferred are the alkaline earth hydroxides because of their additionally greater solubility, and even more preferred are the alkali metal hydroxides. The alkali metal hydroxides are particularly preferred because of their combined greater catalytic activity and greater solubility in the alcohol phase. The most preferred catalyst is sodium hydroxide because of availability, ease of use, cost, catalytic activity, and solubility in the alcohol-based wash fluid. Although it is desirable that water addition to the system be kept at a minimum so as to minimize the generation of spent wash fluid, ease of handling may justify placing the basic metal catalyst in a concentrated form in either an aqueous solution or aqueous slurry prior to make-up of the wash solution.

The required concentration of each component in the wash fluid, that is the alcohol, oxidizing agent, and catalyst is dependent on the degree of impurities in the crude polysulfide product. Because the solubility of unreacted mercaptan in the alcohol phase generally decreases as the mercaptan carbon number increases, correspondingly greater amounts of alcohol are required. For higher carbon number polysulfides, multiple washes may be required. Therefore, the required amount of alcohol, oxidizing agents, and catalyst is that amount effective to convert crude polysulfide to a deodorized, clear product in a stable state suitable for long term storage. It is preferred that the wash fluid consists of at least 50 weight percent alcohol, more preferably 60 to 95 weight percent, and most preferably 70 to 85 weight percent.

The preferred amount of oxidizing agent in the wash fluid is that amount effective to insure oxidation of all unreacted mercaptan to disulfide, all amine catalyst to amine oxide and all hydrogen sulfide to sulfate. The nominal amount is the stoichiometric amount for the reactions of interest. Although wishing not to be bound by the theory, the reaction stoichiometry is generally believed to be:

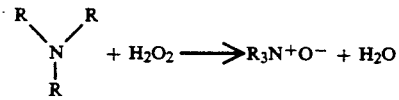

The R groups in the preceding equation are alkyl or arylalkyl radicals and may be the same or different. The most preferred oxidizing agent, as previously noted, is hydrogen peroxide which is generally added via an aqueous solution. It is preferred that the water contribution from the hydrogen peroxide addition be maintained as minimal as reasonably possible so as to minimize the amount of water present in the wash fluid, resulting products, and spent wash fluid. A hydrogen peroxide concentration in water of greater than 20 weight percent is preferred and about or greater than 30 weight percent still more preferred. Most preferred is a hydrogen peroxide concentration of 30 to 35 weight percent because of commercial availability and corresponding ease of use.

The basic metal catalyst should be present in an amount effective to bring about complete oxidation at the designated operating temperature within several hours. Higher temperatures generally favor faster oxidation reactions. However, because of flammability considerations when using alcohols in an oxidizing environment and the potential for undesirable side reactions, temperature is dependent to some degree on the alcohol used and at the discretion of one skilled in the art. When using methanol, a temperature of ambient to 70° C. is preferred and about 45° C. most preferred. A second factor affecting the desired amount of catalyst is the resulting pH of the wash and spent wash solutions and the potential for the catalyst to react directly with the product of the hydrogen sulfide oxidation reaction, a sulfate, and thereby produce a precipitant. Using sodium hydroxide as an example, the overall reactions are generally believed to be:

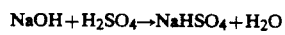

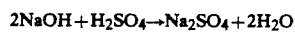

As indicated by the preceding reactions, the inorganic basic catalyst can be consumed. The amount of catalyst will also affect the pH of the spent wash solution which has ramifications in how this waste stream is subsequently handled. As shown in Table III, a factor of 2 change in the amount of inorganic basic catalyst changes the pH of the waste stream from acid (pH of 2) to neutral or slightly basic (pH of 7–11). From an operational, design, and waste treatment perspective, these changes are significant. Therefore, the molar ratio of inorganic basic catalyst to oxidizing agent is preferably 0.1 to 1.5, more preferably about 0.25 to 1.0 and most preferably about 0.3 to about 0.6.

One preferred method for the treatment of crude di-t-nonyl polysulfide containing an average of 5 sulfurs per molecule comprises the batchwise and thorough contacting via vigorous agitation of 57 weight parts of crude product with about 1 weight part 30 weight percent hydrogen peroxide, about 4 weight parts methanol, and about 0.13 weight part sodium hydroxide at 45° C. for 2 hours (see Example I). The corresponding molar ratios of methanol and sodium hydroxide to hydrogen peroxide are about 14.2 and 0.37, respectively.

Although batchwise contacting of the polysulfide/alcohol phases via one or more washes may be preferable for the purification of relatively small quantities of crude polysulfide, extension of said technology to continuous flow systems wherein phase contacting is done via continuous stir tank reactors connecting in series, mixer/settlers Ruston reactors, and packed towers with counter-current flow is readily within the realm of one skilled in the art.

The following examples are provided to illustrate the practice of the invention and are not intended to limit the scope of the invention or the appended claims in any way.

EXAMPLE I

This Example concerns the laboratory-scale synthesis and purification of di-t-nonyl polysulfide using the inventive process herein claimed.

To a 1 liter autoclave reactor which had been flushed with nitrogen ($N_2$) was added a solution of 599 g (3.74 mole) t-nonyl mercaptan and 3.8 g (0.037 mole) triethylamine. The autoclave was heated to 30° C. and the contents were stirred rapidly (1000 rpm). Sulfur (240 g, 7.49 mole) in a 300 ml stainless steel bomb equipped with an internal thermocouple was melted by heating at 120°–135° C. under $N_2$. The $N_2$ pressure above the sulfur was then increased to 200 psi and the valve and tubing between the bomb and autoclave heated to avoid solidification during sulfur transfer. Preferably, the liquid sulfur should be added to the reactant mixture over a 30 minute period, but the current setup required addition over a 2 minute time period so as to avoid solidification of sulfur in the tube that went through the autoclave body. The tube in the reactor body and inside the reactor must be heated in some way to a temperature greater than 120° C. The addition of the liquid sulfur over a 2 minute time period caused the autoclave temperature to increase from 30° C. to the desired process temperature of 45° C. If the sulfur had been added over a 30 minute time period, the autoclave would have initially been heated to 45° C. rather than 30° C.

When the sulfur addition was completed, the autoclave pressure had increased to 150 psi due to $H_2S$ evolution. The pressure showed no tendency to go above this value. The autoclave pressure was then decreased to 60 psi by the controlled venting of $H_2S$. If venting was conducted too fast, foaming occurred. After venting for about 0.5 hour, the pressure did not increase above 60 psi. At this point, $H_2S$ was removed by pressurizing the autoclave with $N_2$ to 100 psi and then venting to 60 psi. This was repeated 3 more times over a 0.5 hour time period. Hydrogen sulfide evolution at this stage was low and the pressure (mainly due to $N_2$) was allowed to decrease to near atmospheric whereupon the system was opened to a vent line. Heating at 45° C. with rapid stirring (1000 rpm) was continued for an additional 1.5 hours (total time after addition of all sulfur was 2.5 hours). Nitrogen was then bubbled (2 std cubic ft/hr) through the reaction mixture at 45° C. with rapid stirring (1000 rpm) for 4 hours.

To the crude product was added a solution of 1.8 g (0.045 mole) sodium hydroxide and 54 g (1.69 mole) methanol. The mixture was heated to 45° C. and 13.5 g of 30 weight percent hydrogen peroxide (0.119 mole) was incrementally added over 15 minutes at 45° C. with rapid stirring. Rapid stirring was continued for an additional 2 hours at 45° C. After cooling, the polysulfide layer (bottom layer) was separated from the methanol layer (top layer). The methanol layer also contained water (from 30 weight percent hydrogen peroxide solution), unreacted hydrogen peroxide, and sulfates of sodium. The polysulfide layer was vacuum stripped with stirring at 5 torr and 45° C. for 2 hours. After cooling, the polysulfide was filtered to give 775 g (100% yield) of a clear yellow liquid. The mercaptan sulfur was 4 ppm by weight in one case and less than 1 ppm in another. Antek nitrogen was less than 2.5 ppm by weight and the material remained a clear yellow liquid for months.

Other runs were conducted where larger amounts of NaOH or $H_2O_2$ were used. Increasing the amount of NaOH by 50–100% or increasing the NaOH and $H_2O_2$ concentrations by 100% were observed to negligibly affect the final product.

EXAMPLE II

Crude product t-nonyl polysulfide was prepared using a procedure similar to that described in Example I. The wash step was conducted in a 500 mL, 3-necked round bottom reactor with condenser, magnetic stirring bar, and a thermowell. Unless otherwise noted, the wash procedure consisted of combining 230 g of crude product with the designated amount of water, methanol and sodium hydroxide presented in Table I and heating said mixture to 45° C. (note exception for Run No. 5) whereupon the aqueous hydrogen peroxide was added and maintained for an additional 4 hrs. In two tests (Runs No. 4 and 5), additional aqueous hydrogen peroxide was added and the elevated temperature maintained for an additional 0.5 hr. The mixture was then cooled and 75 g of the mixture washed by contacting with 100 mL pentane, shaking said mixture for 2 to 3 min., and discarding the lower aqueous phase. The upper phase was then washed with water, dried in a Rotovap at 45° C., and finally vacuumed stripped at 5 torr and 45° C. After cooling, the purified product was filtered twice.

The results of 5 tests are presented in Table I. Only the wash fluid consisting of an alcohol (methanol), an oxidizing agent (30 wt. % hydrogen peroxide) and an inorganic basic catalyst (sodium hydroxide) provided a product with acceptable mercaptan sulfur content (i.e., no odor), acceptable nitrogen content (negligible amine catalyst) and acceptable visual appearance after extending aging (a clear fluid containing negligible precipitant). The absence of either the alcohol or the basic metal catalyst from the wash fluid resulted in unacceptable product.

TABLE I

| Run No. | t-nonyl polysulfide | Aqueous $H_2O_2$ (30 wt %) | Water | Methanol | NaOH | Sulfur Content[a] | Nitrogen Content[b] | Precipitant at ~3 mo. | Haze at ~3 mo. |
|---|---|---|---|---|---|---|---|---|---|
| 1 | 230 gr | 8 gr | 16 gr | 0 gr | 0 gr | 460 ppm | <2.5 ppm | Yes | Yes |
| 2 | 230 | 8 | 0 | 16 | 0 | 242 | <2.5 | No | Very slight |
| 3 | 230 | 8 + 2[c] | 0 | 0 | 2 | 67 | <2.5 | Yes | Yes |
| 4 | 230 | 8 + 2[c] | 0 | 16 | 2 | <1 | 17.7[e] | No | Very slight if at all[d] |

TABLE I-continued

| Run No. | t-nonyl polysulfide | Aqueous H$_2$O$_2$ (30 wt %) | Water | Methanol | NaOH | Sulfur Content[a] | Nitrogen Content[b] | Precipitant at ~3 mo. | Haze at ~3 mo. |
|---|---|---|---|---|---|---|---|---|---|
| 5[f] | 230 | 8 | 0 | 16 | 0 | 219 | — | No | Yes |

[a] Mercaptan sulfur by weight.
[b] Antek nitrogen by weight.
[c] Additional treatment step followed the initial wash and consisted of the addition of 2 gr 30 wt % H$_2$O$_2$ followed by agitation for 0.5 hr at the process temperature.
[d] Measured at 2 months.
[e] This number may be anomolous as numerous similar treatments give nitrogen contents less than 2.5 by weight.
[f] Heating conducted for 4 hrs at 68–70° C. rather than 4 hrs at 45° C.

EXAMPLE III

This example concerns the large-scale synthesis and purification of di-t-nonyl polysulfides using the inventive purification process herein claimed.

Triethylamine catalyst was added to t-nonyl mercaptan at a ratio of 1100 grams of amine to each drum (385 lbs net) of mercaptan. A total of 660 pounds of this mixture was then charged to a 100-gallon Hastelloy C batch reactor 30° C. (86° F.). Sulfur was charged to a jacketed vessel and heated to about 150° C. (300° F.) with a glycol heating system. Since this vessel was of inadequate size to hold the entire 264 pounds of sulfur needed for each batch of di-t-nonyl polysulfide, the sulfur was melted in two steps. When the sulfur was melted, it was transferred to the reactor by pressurizing the sulfur melt tank with nitrogen. The transfer line from the sulfur melt tank to the reactor was heat-traced. Because the sulfur transfer line extended into the reactor by about 8 inches so as to keep the sulfur off the reactor walls, this portion of the line could not be heated and any freezing and plugging problems were expected to occur at that location. Therefore, no attempt was made to control the rate of sulfur addition. By transferring the sulfur at a high rate, the line stayed warm and freezing of the sulfur did not occur in the reactor.

As soon as the sulfur entered the reactor, the reaction began evolving H$_2$S. The pressure in the reactor rose to as high as 192 psig, but part of this pressure increase was caused by the nitrogen used to transfer the molten sulfur. When the sulfur addition had been completed, the evolved H$_2$S was vented through the distillation column and condenser attached to the reactor and then through a knock-out pot and finally to a vent. Because of concern about the possible carryover of condensable liquids by H$_2$S, the knock-out pot was checked after the first two batches and no liquid was found. Because of facility limitations allowing a maximum release rate of 20 lbs/hr of H$_2$S, the minimum length of time for venting the evolved H$_2$S was about 4 hours. This in effect was the time available for reaction which compared to a typical "reaction time" of only two hours for similar tests conducted at the laboratory scale. After H$_2$S venting was completed, nitrogen was bubbled through the product to remove most of the residual H$_2$S. The first two batches were purged for about 12 hours to reduce the H$_2$S content to below about 10 ppm by weight so that the reactor could be opened for inspection to look for sulfur deposits on the reactor walls. When no deposits were observed after the first two batches, it was determined that reduction of the H$_2$S content to such a low level was not required and the nitrogen purge step was then set at 4 hours, as had been used in the laboratory.

When the nitrogen purge step was finished, 95 lbs of crude product was drained out of the reactor so as to reduce the volume of material in the reactor prior to the wash step. To perform the wash step, 4 lbs of 50% aqueous sodium hydroxide was added to the reactor with stirring at 375 RPM, the maximum speed of the mixer, and the reactor temperature was held at 45° C. (113° F.). Following the addition of the sodium hydroxide, 58 lbs of methanol was charged to the reactor. A solution of 35 weight percent hydrogen peroxide was then charged in three increments of 5 lbs each, for a total of 15 lbs. A temperature rise of 12° C. (22° F.) was observed after the addition of the first 5 lbs of peroxide, and smaller increases were observed after the addition of the rest of the peroxide . The laboratory runs indicated a mix time of 2 hours for this step, but it was found after the first two batches (Batch #1 and #2 in Table II) that 2 hours was not sufficient to reduce the mercaptan sulfur content to below 20 ppm by weight. Tests were conducted wherein the mix time was increased to 4 hours and the amounts of caustic and peroxide were increased by 50%. Later, the amount of peroxide was successfully reduced to the original amount of 15 lbs and the mix time was left at 4 hours. This was sufficient to reduce the mercaptan sulfur content to about 15 to 17 ppm by weight (See Table II).

The polysulfide/methanol mixture was allowed to settle for at least one hour with the polysulfide phase on the bottom and the methanol phase on the top. The polysulfide phase was drained to the mix/wash tank, and the methanol phase was put into waste drums. For each lot in Table II, two or three batches of the t-nonyl polysulfide were accumulated in the mix/wash tank which is a 300-gallon, glass-lined Pfaudler reactor. Nitrogen was bubbled through the polysulfide at 45° C. (132° F.) while the product was stirred. The product changed from a cloudy yellow to clear yellow as residual water and methanol were removed. The nitrogen stripping was allowed to continue for at least one hour past the point at which the product became clear. The time required for this step was 3 hours for one lot and 6 hours for the other lot.

When the product was judged to be finished, the product was filtered via cartridge filters and transferred to clean, 55-gallon product drums, each holding 465 lbs net. Any solids remaining on top of the final product were residue from the phase separation and were sent to waste.

Total yield from the t-nonyl polysulfide was 3626 lbs, compared to 4600 lbs expected. The loss is believed to have occurred during the wash step.

TABLE II

| Batch | T-Nonyl Polysulfide Results | | | | |
|---|---|---|---|---|---|
| | 1 | 2 | 3 | 4 | 5 |
| Charge | | | | | |
| mercaptan, lbs(1) | 600 | 660 | 660 | 660 | 660 |
| sulfur, lbs | 240 | 264 | 264 | 264 | 264 |
| Wash Charges and | | | | | |

TABLE II-continued

| | T-Nonyl Polysulfide Results | | | | |
|---|---|---|---|---|---|
| Batch | 1 | 2 | 3 | 4 | 5 |
| Mix Time | | | | | |
| 50% NaOH, lbs | 4 | 6 | 6 | 6 | |
| methanol, lbs | 58 | 58 | 58 | 58 | 58 |
| 35% H$_2$O$_2$, lbs | 15 | 15 | 15 | 15 | 22 |
| Mix Time, hrs | 2 | 2 | 4 | 4 | 4 |
| Composition | | | | | |
| Density, g/cc (2) | 1.026 | 1.027 | 1.020 | 1.021 | 1.023 |
| Nitrogen, ppm (2) | 16.4 | 16.1 | <2.5 | <2.5 | 235 |
| % sulfur, x-ray (2) | 37.3 | 38.1 | 37.3 | 37.6 | — |
| % sulfur, CHNS (3) | — | 40.2 | — | — | — |
| Merc. sulf., ppm (3) | 36 | 32 | — | 15.6 | 19 |
| Blended Composition | Lot 1 (batches 1, 2 & 3) | | | Lot 2 (batches 4 & 5) | |
| Density, g/cc | 1.021 | | | 1.022 | |
| Mercaptan sulfur, ppm (wt) | 8.3 | | | 17 | |
| % Sulfur, CHNS | 38.9 | | | 39.9 | |

Notes:
(1) Mercaptan contained 110 grams of triethyl amine per 385 lbs of mercaptan.
(2) Before wash step. Nitrogen content determined by Antek method and is given on a nitrogen weight basis.
(3) After wash step. Batches 1, 2 and 3 were washed again to lower the mercaptan sulfur content.
(4) % sulfur, CHNS determined via combustion analysis for carbon, hydrogen, nitrogen and sulfur. Value given is on a weight basis.
(5) % sulfur, x-ray determined using x-ray fluorescence wherein concentration of polysulfide product in reagent-grade toluene was about 1%. Value given is on a weight basis.

EXAMPLE IV

This Example concerns the large-scale synthesis and purification of di-t-dodecyl polysulfide using the inventive process herein claimed.

The t-dodecyl polysulfide was produced using solid sulfur. Solid sulfur was shown (by laboratory work) to give product equivalent to molten sulfur, and so solid sulfur was used in the pilot plant for this product as a matter of convenience.

Solid sulfur was charged to the 100-gallon reactor first, in the amount of 200 lbs. Next, 634 lbs of t-dodecyl mercaptan was charged to the reactor, and the reactor was heated to 30° C. (86°) with full stirring (375 rpm).

The triethylamine was charged to the reactor from a small charge pot by pressurizing the pot with nitrogen. As soon as the amine was added, the reaction began and H$_2$S was evolved. Again, as in Example III, the H$_2$S was vented slowly and the venting rate was again limited to 20 lbs per hour or less by facility limitations. Nitrogen was bubbled through the product for 4 hours to remove H$_2$S.

To perform the wash step, 6 lbs of aqueous 50% sodium hydroxide was added to the reactor, followed by 58 lbs of methanol, followed by three increments of 5 lbs each of 35% hydrogen peroxide, similar to what was done with the t-nonyl polysulfide (See Example III). For the last three batches, the amount of sodium hydroxide was doubled to 12 lbs in order to raise the pH of the methanol solution to near a neutral value of 7. Of the three batches done this way, the pH of the methanol phase was 11, 10 and 6. It was thought that the higher amount of caustic might create an emulsion and make the phase separation difficult, but the phase separation was no more difficult than with the lower amount of caustic. Following the phase separation, the procedure of Example III was followed wherein nitrogen was bubbled through the polysulfide phase and the product was then filtered and transferred to appropriate vessels for storage.

Total yield from the t-dodecyl polysulfide was 3678 lbs, compared to 4170 lbs expected. The loss is believed to have occurred during the wash step. Experimental results concerning the preparation of 5 batches of t-dodecyl polysulfide are presented in Table III.

TABLE III

| | T-Dodecyl Polysulfide Results | | | | |
|---|---|---|---|---|---|
| Batch | 1 | 2 | 3 | 4 | 5 |
| Charge | | | | | |
| mercaptan, lbs. | 634 | 634 | 632 | 632 | 634 |
| triethyl amine, g | 650 | 865 | 865 | 874 | 870 |
| sulfur, lbs | 200 | 200 | 200 | 200 | 200 |
| Wash Charges and Mix Time | | | | | |
| 50% NaOH, lbs | 6 | 6 | 12 | 12 | 12 |
| methanol, lbs | 58 | 58 | 58 | 58 | 58 |
| 35% H$_2$O$_2$, lbs | 15 | 15 | 15 | 15 | 15 |
| Mix Time, hrs | 4 | 4 | 4 | 4 | 4 |
| pH of methanol | — | 2 | 11 | 10 | 7 |
| Composition | | | | | |
| Density, g/cc (1) | 1.005 | 1.009 | 1.007 | — | 0.999 |
| Nitrogen, ppm (1) | 27.4 | 39.5 | 47.9 | — | <2.4 |
| Blended Composition | Lot 1 (batches 1 & 2) | | Lot 2 (batches 3, 4, & 5) | | |
| Density, g/cc | 0.992 | | 0.990 | | |
| Mercaptan sulfur, ppm (wt) | 662. | | 8.8 | | |
| Sulfur, CHNS | 30.6 | | 31.1 | | |
| Sulfur, x-ray | 31.5 | | 29.8 | | |

Notes:
(1) Before wash step. Nitrogen content determined by Antek method.
(2) Lot 1 needs to be washed again.
(3) Sulfur, CHNS determined via combustion analysis for carbon, hydrogen, nitrogen and sulfur. Value given is on a weight basis.
(4) % Sulfur, x-ray determined using x-ray fluorescence wherein concentration of polysulfide product in reagent-grade toluene was about 1%. Value given is on a weight basis.

That which is claimed is:

1. A process for purifying a polysulfide comprising the steps of:
    (a) contacting said polysulfide with an alcohol-based wash solution comprising at least 50 wt % alcohol, an oxidizing agent which has some solubility in said alcohol and negligible solubility in said polysulfide, and an inorganic basic catalyst to give a washed polysulfide-bearing lower phase and a spent wash solution upper phase;
    (b) separating said washed polysulfide-bearing lower phase from said spent wash solution upper phase to obtain a washed polysulfide and a spent wash solution; and
    (c) recovering from said washed polysulfide a purified polysulfide product.

2. A process according to claim 1, wherein said alcohol contains 1 to 5 carbon atoms.

3. A process according to claim 2, wherein said oxidizing agent is selected from the group consisting of peracids, hypochlorites, persulfates, hydroperoxides, organic peroxides, oxygen, ozone and hydrogen peroxide.

4. A process according to claim 3, wherein said basic metal catalyst is selected from the group consisting of alkali metal carbonates, alkaline earth carbonates, alkali metal oxides, alkaline earth oxides, alkali metal hydroxides, alkaline earth hydroxides, and the hydrates thereof.

5. A process according to claim 4, wherein said alcohol is selected from the group consisting of 1-propanol, isopropanol, ethanol, and methanol.

6. A process according to claim 5, wherein said oxidizing agent is aqueous hydrogen peroxide.

7. A process according to claim 6, wherein said basic metal catalyst is selected from the group consisting of alkali metal hydroxides, alkaline earth hydroxides and the hydrates thereof.

8. A process according to claim 7, wherein said basic metal catalyst is selected from the group consisting of alkali metal hydroxides.

9. A process according to claim 1, wherein said recovery includes removing alcohol and water from said washed polysulfide thereby obtaining said purified polysulfide product.

10. A process according to claim 9, wherein said alcohol is methanol, said oxidizing agent is aqueous hydrogen peroxide, and said basic metal catalyst is sodium hydroxide.

11. A process according to claim 9, wherein said removing is conducted with a gas purge.

12. A process according to claim 11, wherein said removing is conducted with a gas purge.

13. A process according to claim 9, wherein said removing is conducted via vacuum stripping.

14. A process according to claim 10, wherein said removing is conducted via heating.

15. A process according to claim 1, further comprising filtering said purified polysulfide to remove residual solids.

16. A process according to claim 10, further comprising filtering said purified polysulfide to remove residual solids.

17. A process according to claim 1, wherein said polysulfide is made by contacting elemental sulfur with at least one alkyl mercaptan containing 1 to 20 carbon atoms in the presence of a basic catalyst selected from the group consisting of primary alkyl amines, secondary alkyl amines, tertiary alkyl amines, cycloaliphatic amines, alkali metal oxides, alkaline earth oxides, alkali metal hydroxides and alkaline earth hydroxides, and wherein the weight of said catalyst as a percentage of the weight of said mercaptan is 0.05 to 5% to make a crude polysulfide product and removing hydrogen sulfide from said crude product to obtain said polysulfide wherein said removing step is selected from the group consisting of heating, inert gas purging and vacuum stripping.

18. A process according to claim 10, wherein said polysulfide is made by contacting elemental sulfur with at least one alkyl mercaptan containing 1 to 20 carbon atoms in the presence of a basic catalyst selected from the group consisting of primary alkyl amines, secondary alkyl amines, tertiary alkyl amines, cycloaliphatic amines, alkali metal oxides, alkaline earth oxides, alkali metal hydroxides and alkaline earth hydroxides, and wherein the weight of said catalyst as a percentage of the weight of said mercaptan is 0.05 to 5% to make a crude polysulfide product and further comprising the step of removing hydrogen sulfide from said crude product to obtain said polysulfide wherein said removing step is selected from the group consisting of heating, inert gas purging and vacuum stripping.

19. A process according to claim 1, wherein said polysulfide is made by contacting elemental sulfur with $C_4$–$C_{18}$ tertiary alkyl mercaptans in the presence of an amine-based catalyst to make a crude polysulfide product and further comprising the step of removing hydrogen sulfide from said crude product to obtain said polysulfide wherein said removing step is selected from the group consisting of heating, inert gas purging and vacuum stripping.

20. A process according to claim 10, wherein said polysulfide is made by contacting elemental sulfur with $C_4$–$C_{18}$ tertiary alkyl mercaptans in the presence of an amine-based catalyst to make a crude polysulfide product and further comprising the step of removing hydrogen sulfide from said crude product to obtain said polysulfide wherein said removing step is selected from the group consisting of heating, inert gas purging and vacuum stripping.

21. A process according to claim 1, wherein said polysulfide is made by contacting elemental sulfur with $C_9$–$C_{12}$ tertiary alkyl mercaptans in the presence of an amine-based catalyst to make a crude polysulfide product and further comprising the step of removing hydrogen sulfide from said crude product to obtain said polysulfide wherein said removing step is selected from the group consisting of heating, inert gas purging and vacuum stripping.

22. A process according to claim 10, wherein said polysulfide is made by contacting elemental sulfur with $C_9$–$C_{12}$ tertiary alkyl mercaptans in the presence of an amine-based catalyst to make a crude polysulfide product and further comprising the step of removing hydrogen sulfide from said crude product to obtain said polysulfide wherein said removing step is selected from the group consisting of heating, inert gas purging and vacuum stripping.

23. A process for purifying a di-t-nonyl polysulfide comprising the steps of:
(a) contacting said polysulfide with a wash solution comprising at least 50 wt % methanol, aqueous hydrogen peroxide, and sodium hydroxide catalyst to give a washed polysulfide lower phase and a spent wash solution upper phase;
(b) separating said washed polysulfide lower phase from said spent wash solution upper phase to obtain a washed polysulfide and spent wash solution; and
(c) removing said washed polysulfide of residuals, such as alcohol and water, to obtain a purified polysulfide.

24. A process according to claim 23, wherein said polysulfide is prepared by
(d) contacting stoichiometric amounts of elemental sulfur with t-nonyl mercaptans in the presence of triethylamine catalyst to form a crude di-t-nonyl polysulfide product with an average of 5 sulfur atoms per polysulfide molecule and hydrogen sulfide; and
(e) removing hydrogen sulfide from said crude polysulfide product to obtain said polysulfide wherein said removing step is selected from the group consisting of heating, inert gas purging and vacuum stripping.

25. A process according to claim 24, wherein said hydrogen sulfide is removed by gas purging.

26. A process according to claim 24, wherein said hydrogen sulfide is removed by vacuum stripping.

27. A process according to claim 24, wherein said hydrogen sulfide is removed by heating.

28. A process for purifying a di-t-dodecyl polysulfide comprising the steps of:
(a) contacting said polysulfide with a wash solution comprising at least 50 wt % methanol, aqueous hydrogen peroxide, and sodium hydroxide catalyst to give a washed polysulfide lower phase and a spent wash solution upper phase;
(b) separating said washed polysufide lower phase from said spent wash solution upper phase to obtain a washed polysulfide and a spent wash solution; and (c) removing said washed polysulfide of residuals, such as alcohol and water, to obtain a purified polysulfide wherein said removing step is selected from the group consisting of heating, inert gas purging and vacuum stripping.

29. A process according to claim 28, wherein said polysulfide is prepared by (d) contacting stoichiometric amounts of elemental sulfur with t-nonyl mercaptans in the presence of triethylamine catalyst to form a crude di-t-dodecyl polysulfide product with an average of 5 sulfur atoms per polysulfide molecule and hydrogen sulfide; and (e) removing hydrogen sulfide from said crude polysulfide product to obtain said polysulfide wherein said removing step is selected from the group consisting of heating, inert gas purging and vacuum stripping.

30. A process according to claim 29, wherein said hydrogen sulfide is removed by gas purging.

31. A process according to claim 29, wherein said hydrogen sulfide is removed by vacuum stripping.

32. A process according to claim 29, wherein said hydrogen sulfide is removed by heating.

* * * * *

UNITED STATES PATENT AND TRADEMARK OFFICE
CERTIFICATE OF CORRECTION

PATENT NO. : 5,206,439
DATED : April 27, 1993
INVENTOR(S) : James E. Shaw

It is certified that error appears in the above-identified patent and that said Letters Patent is hereby corrected as shown below:

Column 13, line 18, please delete "claim 11" and insert therefor --- claim 10 ---.

Signed and Sealed this

Twenty-eighth Day of December, 1993

Attest:

BRUCE LEHMAN

Attesting Officer

Commissioner of Patents and Trademarks